(12) United States Patent
Sanborn

(10) Patent No.: US 8,558,018 B2
(45) Date of Patent: Oct. 15, 2013

(54) OXIDATION OF FURFURAL COMPOUNDS

(75) Inventor: Alexandra Sanborn, Lincoln, IL (US)

(73) Assignee: Archer Daniels Midland Company, Decatur, IL (US)

( * ) Notice: Subject to any disclaimer, the term of this patent is extended or adjusted under 35 U.S.C. 154(b) by 191 days.

(21) Appl. No.: 13/319,877

(22) PCT Filed: May 14, 2010

(86) PCT No.: PCT/US2010/034856
§ 371 (c)(1),
(2), (4) Date: Nov. 10, 2011

(87) PCT Pub. No.: WO2010/132740
PCT Pub. Date: Nov. 18, 2010

(65) Prior Publication Data
US 2012/0059178 A1    Mar. 8, 2012

Related U.S. Application Data

(60) Provisional application No. 61/178,301, filed on May 14, 2009.

(51) Int. Cl.
*C07D 307/48* (2006.01)

(52) U.S. Cl.
USPC .......................................................... 549/485

(58) Field of Classification Search
USPC .......................................................... 549/485
See application file for complete search history.

(56) References Cited

U.S. PATENT DOCUMENTS

| | | | |
|---|---|---|---|
| 2,917,520 A | 12/1959 | Cope | |
| 4,977,283 A | 12/1990 | Leupold et al. | |
| 2003/0055271 A1 | 3/2003 | Grushin et al. | |
| 2006/0142599 A1 | 6/2006 | Sanborn et al. | |
| 2010/0218415 A1 | 9/2010 | Gruter et al. | |

OTHER PUBLICATIONS

Partenheimer et al; Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/ Bromide Catalysts; Adv. Synth Catal.; 2001; 343, pp. 102-111.
Halliday et al; One-Pot, Two-Step, Practical Catalytic Synthesis of 2,5-Diformylfuran from Fructose; Organic Letters; 2003, vol. 5, No. 11, pp. 2003-2005.
Bonner et al; The Iodine-catalysed Conversion of Sucrose into 5-Hydroxy-methylfurfuraldehyde; Royal Holloway College, Sep. 14, 1959, pp. 787-791.
Lichtenthaler; Towards improving the utility of ketoses as organic raw materials; Institute for Organic Chemistry, Germany; Apr. 15, 1998, pp. 69-89.
Gandini et al; Furans in Polymer Chemistry; Prog. Polym. Sci., vol. 22, pp. 1203-1379, 1997 Elsevier Science Ltd.
Kunz; Hydroxymethylfurfural, A Possible Basic Chemical for Industrial Intermediates; A. Fuchs (Ed.) Inulin and Inulin-containg Crops, 1993, Elsevier Science Publishers B.V., pp. 149-160.
Antal et al; Mechanism of Formation of 5-(hydroxymethyl)-2-Furalde-hyde from D-fructose and sucrose; Carbohydrate Research, 1990, pp. 91-109, Elsevier Science Publishers B.V.
Kuster et al; 5-Hydroxymethylfurfural (HMF) A review focussing on its manufacture; starch/stark 42 (1990) No. 8 pp. 314-321 VCH D-6940 Weinheim 1990.
International Search Report; Korean Intellectual Property Office, Jan. 25, 2011, PCT/US2010/034856, pp. 1-3.
Written Opinion; Korean Intellectual Property Office, Jan. 24, 2011, PCT/US2010/034856, pp. 1-3.

*Primary Examiner* — Taofiq A Solola
(74) *Attorney, Agent, or Firm* — Alexandra Sanborn; Mark W. Roberts

(57) ABSTRACT

The disclosure pertains to a process for oxidation of furan aldehydes such as 5-hydroxymethyl)furfural (HMF) and derivatives thereof such as 5-(alkoxymethyl)furfural (AMF), 5-(aryloxymethyl)furfural, 5-(cycloalkoxy-methyl)furfural and 5-(alkoxycarbonyl)furfural compounds in the presence of dissolved oxygen and a Co(II), Mn(II), Ce(III) salt catalyst or mixtures thereof. The products from HMF can be selectively chosen to be predominantly 2,5-diformylfuran (DFF), particularly by inclusion of an aliphatic ketone, like methyl ethyl ketone, or can be further oxidized to 2,5-furandicarboxylic acid (FDCA) by the omission of methyl ethyl ketone and inclusion of bromide. When the reactant is an ether derivative of HMF the products are surprisingly ester derivatives where either both the ether and aldehyde functional groups have been oxidized or just the ether function group thereby producing one or both of 5-ester-furan-2-acids (i.e., 5-alkoxycarbonylfurancarboxylic acids) or 5-ester-furan aldehydes, (i.e., -alkoxycarbonylfurfurals a. k. a, 5-(alkoxycarbonyl)furfural). (I).

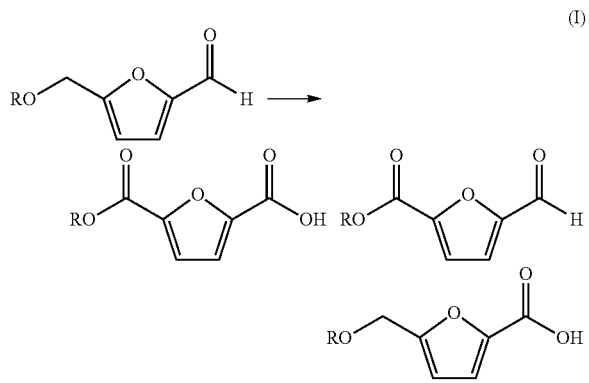

19 Claims, No Drawings

OXIDATION OF FURFURAL COMPOUNDS

PRIORITY

This application claims priority to U.S. provisional application No. 61/178,301 filed May 14, 2009, which is incorporated herein by reference in its entirety.

FIELD OF INVENTION

The invention pertains to processes for oxidation of furan aldehydes such as 5-(hydroxymethyl)furfural (HMF) to selectively form 2,5-diformylfuran (DFF) and to oxidation of ether derivatives of HMF such as 5-(alkoxymethyl)furfural (AMF), 5-(aryloxymethyl)furfural, 5-(cycloalkoxymethyl) furfural and 5-(acyloxymethyl)furfural compounds to form ester-acid derivatives of HMF, particularly 5-(alkoxycarbonyl)furan-2-carboxylic acids. The oxidations are done or in the presence of dissolved oxygen and a Co(II), Mn(II), Ce(III) salt catalyst or mixtures thereof with or without bromide and with or without an aliphatic ketone to selectively form the desired compounds. The products can be further oxidized for form 2,5 furandicarboxylic acid (FDCA).

BACKGROUND

HMF is an important compound with many industrial applications such as use in polymers, solvents, surfactants, pharmaceuticals, and plant protection agents. However, the oxidation derivatives of HMF also have important commercial value. For example, 2,5 diformylfuran (DFF) has various useful applications such as a monomer; as a starting material for the synthesis of drugs, antifungal agents, nematocides and ligands; in photography; and as a cross-linking agent for polyvinyl alcohol. 2,5 furandicarboxylic acid a.k.a. furandiacid (FDCA a.k.a FDA) represents one key intermediate substance and is a suitable starting source for the formation of various furan monomers required for the preparation of non-petroleum-derived polymeric materials.

Many methods have been proposed for making DFF and FDCA. However, these reactions provide low yields, poor selectivity and are not environmentally friendly. For example, it is known that the synthesis of DFF from fructose can be done in a two step process, namely, by dehydration of fructose in a high boiling solvent such as dimethylsulfoxide (DMSO) to form HMF, followed by in situ catalytic air oxidation also in the presence of DMSO to form a mixture of DFF, FDCA and various other reaction side products.

Also, it has been shown that DFF or FDCA could be made from HMF by oxidation in the presence of dissolved oxygen at about 1000 psi, and a catalyst system containing Co(II), Mn(II), and a Br salt preferentially also including Zi (W. Partenhemier & V Grushin: *Adv. Synth. Catal.* (2001) 343, 102-111). However the selectivity for DFF was at most 69% in a catalyst system of Co/Mn/Br, and at most 73%. in a catalyst system of Co/Mn/Br/Zr. The best selectivity for FDCA was 73% in a catalyst system of Co/Mn/Br/Zr and at most about 35% with the same catalyst system but without the Zr. The ability to convert HMF into one predominant oxidation product is difficult due to the reactivity of the aldehyde and alcohol moieties of the HMF molecule. In the above mentioned reference, selectivity between DFF and FDCA as the predominant product was affected by using lower reaction temperatures (50-75° C.) for making DFF, and higher reaction temperatures for making FDCA (typically 100-125° C.).

FDCA is a difficult product to handle. It tends to precipitate in solvents used for oxidation when the temperature is raised and tends to co-precipitate with side products. It would be beneficial if an FDCA precursor could be made that is easy to separate and which could subsequently be converted to FDCA in a different reaction. Also it would be beneficial to find other routes to selective preparation of DFF versus FDCA by oxidative methods. The present invention provides for these and other needs that will be apparent from the description that follows.

SUMMARY OF THE INVENTION

The present invention is based at least in-part, on the surprising discovery that 5-ethers of HMF can be simultaneously oxidized at the ether linkage and at aldehyde to form 5-ester furanic acids, (i.e., 5-alkoxycarbonylfurancarboxylic acids, furan-2,5-dicarboxylic acid monoesters, a.k.a. 5-alkoxycarbonylfuran 2-carboxylic acids) using a catalyst system comprised of Co(II), Mn(II) and Ce(III) salts. These ester compounds are easy to separate by conventional solvent extraction or distillation and can be subsequently converted to FDCA under mild hydrolysis conditions.

It also has been surprisingly found that under similar reaction conditions, HMF can be selectively converted to DFF by the inclusion of a aliphatic ketone, exemplified by methyl ethyl ketone (MEK). The omission of bromide from the reaction mixture also favors selective production of DFF. Conversely, it also has been found that FDCA can be selectively made from HMF at greater than 40% by the inclusion of bromide in the reaction mixture. It also has been found that selective production of FDCA can occur without need for a zirconium co-catalyst in the reaction mixture. It also has been found that HMF can be converted to FDCA using only cobalt, or only cerium salts in the presence of bromide, without the need for manganese or zirconium co-catalyst.

More specifically, the present invention provides methods of oxidizing furan aldehydes that includes heating the furan aldehyde in a reaction mixture comprising a solvent containing dissolved oxygen and at least one catalyst selected from the group consisting of Co(II), Mn(II) and Ce(III) salts. If the furan aldehyde is -5-(hydroxymethyl)furfural., the reaction mixture includes a aliphatic ketone which helps make the predominant reaction product of diformylfuran. If the furan aldehyde is a 5-ether of the furan aldehyde, the predominant reaction product is at least one of a 5-ester furan 2-acid and a 5-(alkoxycarbonyl)furfural. Moreover, if the furan aldehyde is a 5-(alkoxycarbonyl)furfural the predominant reaction product is the 5-ester furan 2-carboxylic acid, meaning that under prolonged reaction conditions, even if 5-(alkoxycarbonyl)furfural or 5-(alkoxymethyl)furoic acid is made from the furan ether aldehyde, intermediate furan can further be oxidized to the ester-acid derivative. The 5-ether of the furan aldehyde can be any ether, especially including a 5-(alkoxymethyl)furfural, a 5-(aryloxymethyl)furfural, and a 5-(cycloalkoxymethyl)furfural. Examples are provided when the furan aldehyde is HMF, and where the 5-ether of the furan aldehyde is 5-(acetoxymethyl)furfural and 5-(butoxymethyl) furfural.

Under typical conditions the reaction mixture is heated to a temperature of between 80° C. and 130° C. at a pressure of oxygen or air of about 600- to about 1000 psi for a time sufficient to form the predominant reaction product. Preferably the temperature is between 100° C. and 125° C., and most typically is about 120° C. Air or oxygen can be used under the pressure conditions to supply oxygen to the reaction mixture. In exemplary embodiments, the reaction mixture contains acetic acid as a principle solvent.

In most desirable embodiments, at least 90% of the furan aldehyde is oxidized into reaction products, and the predominant reaction product is at least 80% of the reaction products. When ester furan aldehydes are used, the predominant reaction product is a 5-ester furan 2-carboxylic acid which can be collected by precipitation from, or evaporation of the reaction mixture in a first purification step. In a second purification step, the precipitate is dissolved in a solvent in which the predominant product has higher solubility than FDCA. in a second purification step. Suitable solvents include, but are not limited to: ethyl acetate, dimethylformamide, dimethylacetate, tetrahydrofuran, dioxane, methyl ethyl ketone, methyl isobutyl ketone, acetonitrile, methyltetrahydrofuran, and C1-C6 alcohols.

rotor. As a result, there is frequent shut down time making the operation inefficient. Prior work has been performed with distillation and the addition of a non-volatile solvent like PEG-600 to prevent the buildup of solid humin polymers. Unfortunately, the use of polyglycols leads to the formation of HMF-PEG ethers.

Due to the instability and limited applications of HMF, the inventor's studies have broadened to include the synthesis and purification of a variety of HMF derivatives. In a first embodiment, derivatives of particular interest are the oxidized forms of HMF, in which HMF is selectively oxidized to form 2,5-diformylfuran (DFF) or 2,5-furandicarboxylic acid (FDCA).

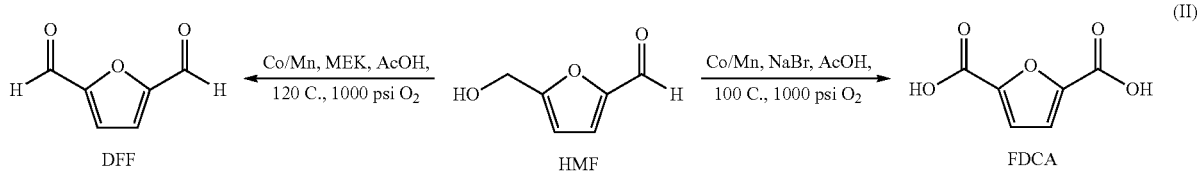

(II)

The catalyst salt can have any typical anion partner, such as acetate, acetate hydrate, bromide, chloride, fluoride, iodide, alkoxide, azide, oxalate, carbonate, carboxylate, hydroxide, nitrate, borate, oxide, acetylacetonate and mixtures thereof.

In certain practices the reaction mixture can include $CO_2$ expanded in the principle solvent of the reactions mixture, for example, $CO_2$ expanded acetic acid. The $CO_2$ should be expanded in the solvent at a pressure of at least 100 psi. Under typical conditions, the oxygen is provided by oxygen gas or air dissolved in the solvent at a pressure of at least 200 psi and $CO_2$ is expanded in the solvent at a pressure of at 100 psi, typically 100-200 psi.

The reaction mixture may also include bromide when it is desirable to form FDCA as a co-product of the oxidizing in which case, under prolonged conditions, FDCA can become the predominant product when HMF, or even the ether derivative of HMF is the reactant. Conversely, and the reaction mixture omits bromide, contains methyl ethyl ketone with HMF as the reactant, the predominant reaction product is DFF.

DETAILED DESCRIPTION OF THE INVENTION

The invention is directed to a low cost and environmentally friendly method for oxidation of a furfural compounds in the presence of oxygen in a reaction mixture containing at least one of Co(II), Mn(II), Ce(III) salt catalysts according to the following reaction scheme:

Other embodiments of particular interest are oxidation of ethers of HMF a.k.a, 5-alkoxymethylfurfurals.(AMF). In past work, the inventor has been able to obtain overall high yields of AMF by acid dehydration of fructose using crystalline fructose and even high fructose corn syrup (HFCS) in the first step shown in the reaction below. The ether derivatives can be easily formed, are more stable, and can be separated making them even more useful than HMF itself.

With the present invention, however, oxidation of AMF can also readily be achieved using the same catalyst as used for oxidizing HMF. The major resulting product is surprisingly found to be ester derivative a 5-(alkoxycarbonyl)furancarboxylic acid (AcMF) where the alkoxymethyl ether linkage has been oxidized to an ester and while the furan aldehyde is oxidized to the acid shown at the right of the reaction below.

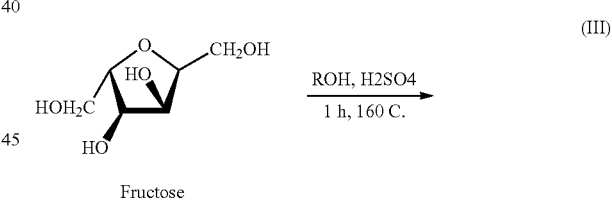

(III)

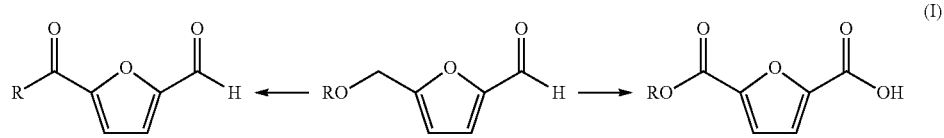

(I)

wherein R represents H, alkyl, aryl, acyl, cycloalkyl or alkylcarbonyl.

The purification of HMF has proved to be a troublesome operation. On long exposure to temperatures at which the desired product can be distilled, HMF and impurities associated with the synthetic mixture, tend to form tarry degradation products. Because of this heat instability, a falling film vacuum still must be used. Even in such an apparatus, resinous solids form on the heating surface causing a stalling in the -continued

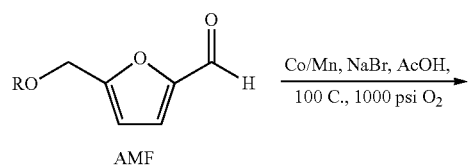

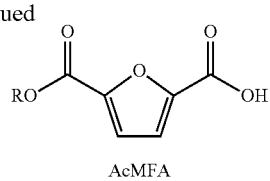

AcMFA

The benefit of the ester derivative is that unlike FDCA, the ester derivative is readily soluble in a variety of organic compounds while FDCA is highly insoluble. The ester derivatives, however, can readily be hydrolyzed in the presence of acid or base catalysts, or further oxidized to provide FDCA when FDCA is ultimately the desired product. Because the differential solubility and ease of handling, formation of the ester acid derivative can improve upstream purification processes and yields when it is desired to ultimately obtain FDCA.

In one embodiment of the invention, HMF (crude or pure) is heated in a solvent in the presence of Co(II) and/or Mn(II) salt catalysts with dissolved oxygen or air. The reaction can proceed to selectively form 2,5-diformylfuran (DFF) by inclusion of an aliphatic ketone, like methyl ethyl ketone and omission of a bromide promoter in the reaction mixture. The reaction will selectively go to or 2,5-furandicarboxylic acid (FDCA) by inclusion of the bromide and omission of the aliphatic ketone in accordance with reaction scheme (II) above. Higher reaction temperatures will drive the reaction to carboxylic acids.

In certain embodiments: it is preferred to use a $CO_2$ expanded liquid (CXL) as the solvent for the reaction mixture. A CXL, is generated by mixing nontoxic, nonflammable carbon dioxide with either a conventional organic solvent or a binary mixture of the organic solvent and water to form a single-phase liquid. The resulting CXL greatly reduces the potential for forming explosive vapors and possesses properties desirable as a medium for performing catalytic reactions. CXLs improve the solubility of liquid and gaseous reactants, as well as catalysts salts, and improve mass transfer compared to traditional pure liquid-phase reactions. Additionally, CXLs reduce the usage of organic solvents and thereby the emissions of organic vapors into the atmosphere. For these reasons, CXL solvents are attractive for many reactions.

Most solvents are miscible and can be expanded with $CO_2$. Preferred solvents for the reactions of the present invention are polar organic solvents, which include, but are not limited to, carboxylic acids such as acetic acid and alcohols such as ethanol and methanol, and organic solvents such as acetonitrile, acetone, n-methylpyrrolidinone, methylene chloride, methyl ethyl ketone, methyl isobutyl ketone or combinations thereof. Aqueous mixtures of these solvents may also be included.

The reaction includes one or more Co(II), Mn(II), Ce(III) salt catalysts. The anion of salts can be in many forms, typically those selected from the group consisting of an acetate, acetate hydrate, bromide, chloride, fluoride, iodide, alkoxide, azide, oxalate, carbonate, carboxylate, hydroxide, nitrate, borate, oxide, acetylacetonate salts of cobalt, cerium and manganese. The acetate salt of Co(II) in combination with Mn(II) are used in most of the exemplary embodiments disclosed herein, however, Co(II) alone or Ce(III) are also shown to work, and other slats of one or more of these metals in various combinations should also catalyze the oxidation reactions.

For each reaction, the mixture is heated under mild pressure (Exemplified at 600-1000 psi), and the reactions proceed rapidly. Bromide is favored for the production of FDCA, however FDCA will also be made in the absence of the bromide promoter. The elimination of the bromide promoter in the formation of FDCA makes the reaction system less corrosive and more economical. It also has been surprisingly found, that unlike the sytem described by W. Partenhemier & V Grushin: Adv. Synth. Catal. (2001) 343, 102-111), zirconium is not required for selective oxidation to FDCA at high molar yields, Catalyst systems containing only cobalt and bromide or only cerinium and bromide, or the combination of cobalt, manganese and bromide salts can all make FDCA at high molar yields.

For each reaction, the mixture is heated, typically to between 100-130° C., more typically between 110-125° C., and most typically to about 120° C. under mild pressure (typically 800-1000 psi), and the reactions proceed rapidly. Also, the oxidization to FDCA can be advantageously achieved by using dense CXLs. Dense CXLs refers to the production of $CO_2$ expanded liquids by condensing relatively large amounts of $CO_2$ into fixed amounts of a polar organic solvent. Typically the $CO_2$ is expanded into the principle solvent of the reaction mixture at 100-200 psi. The advantage is that a large amount of $CO_2$ favors oxygen solubility while polar organic solvents favor catalyst solubility. The combination of dense $CO_2$ and polar organic solvents enables mild conditions and reasonable reaction times. Thus, the method of present invention allows for a cost effective approach towards the synthesis of FDCA from HMF.

By using $CO_2$ expanded acetic acid solvent, the reaction should occur under milder conditions. For example, conditions to form DFF from HMF without the use of $CO_2$ expanded acetic acid solvent uses pressures of at least about 800-1000 psi oxygen as shown in Examples 1-4. However, when $CO_2$ expanded acetic acid solvent is used, the pressure can be lowered to 100-200 psi oxygen and 100-200 psi $CO_2$. Also, the amount of organic solvent is reduced leading to an environmentally friendly and efficient process. In addition, the solubility of oxygen in the $CO_2$-expanded liquid is improved by the presence of $CO_2$ resulting in shorter reaction times.

In one practice of the invention, a sugar can be converted directly to DFF. HMF can be obtained from sugar sources including crystalline fructose and high fructose corn syrup. HMF is prepared by dehydrating a sugar in the presence of an sulfuric acid and a organic solvents such as acetonitrile, acetone, N-methylpyrrolidinone (NMP), methylene chloride, dimethylacetamide, and dimethylformamide for 1 to 3 hours at a temperature from about 170 to about 250° C. and then oxidized to DFF in the presence of oxygen, methyl ethyl ketone and the Co/Mn catalysts as set forth in the reaction scheme (III) below:

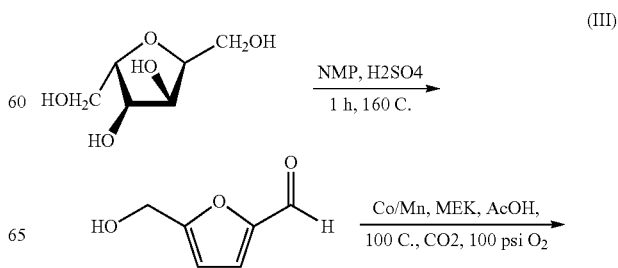

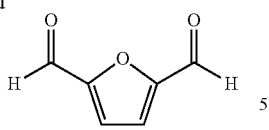

In still more advantageous embodiments, the starting material can be ethers of HMF including any of 5-(aryloxymethyl) furfural, 5-(cycloalkoxy-methyl)furfural and 5-(alkoxycarbonyl)furfural. These starting materials can be in a pure or crude form. The reaction conditions are substantially the same as those for the oxidation of HMF to FDCA and surprisingly proceeds to an ester acid derivative in accordance with the following reaction scheme.

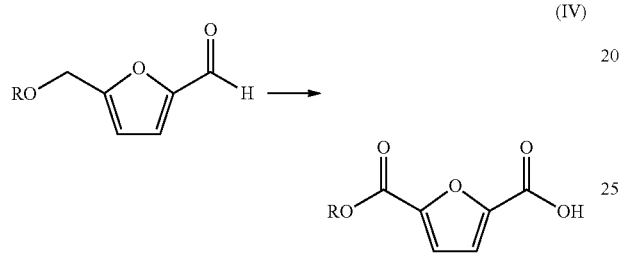

Where R represents H, alkyl, aryl, cycloalkyl or alkylcarbonyl.

The resulting ester acids can be easily purified from the reaction mixture by precipitation from, or evaporation of the reaction mixture. The precipitation can be conducted by lowering the reaction mixture to room temperature or below for a time sufficient to precipitate the ester furan acid derivative in a first purification step. Any FDCA formed in the reaction mixture will tend to co precipitate with the ester furan acid derivative, however, FDCA is not as soluble in many solvents as the ester furan acid. Accordingly, a second purification step is to redissolve the precipitate in a solvent in which FDCA is less soluble than the ester furan acid derivative. Suitable solvents include, but are not limited to, ethyl acetate, dimethylformamide, dimethylacetate, tetrahydrofuran, dioxane, methyl ethyl ketone, methyl isobutyl ketone, acetonitrile, methyltetrahydrofuran, and C1-C6 alcohols. The recovered ester furan acid derivative can be subsequently hydrolyzed in the presence of a heterogenous or homogenous acid or base catalyst, or subsequently further oxidized to yield FDCA and the R-alcohol co-product, which can be recovered for reuse.

EXAMPLES

Only a few examples of the present disclosure are shown herein, it is to be understood that the disclosure is capable of practice in various combinations and with any of the materials described in the specification. Thus, while the Examples illustrate use of a cobalt acetate catalyst in combination with manganese acetate, the catalyst could just as well be cobalt alone, manganese or cerium alone, or in other combinations, and the anion of the salt could be any of those previously mentioned herein. Similarly, the solvent system in the examples is always, acetic acid and includes methyl ethyl ketone. This is for consistency of comparison, and the invention can just well be practices with any of the solvents previously described. Accordingly, the examples are provided for illustrative purposes and no limitation of the invention is implied by the materials and conditions of the examples.

Selective Oxidation of HMF to DFF Using Co/Mn Catalysts in the Presence of Methyl Ethyl Ketone

Example 1

A reaction mixture containing 97% purity HMF (5.0 g), acetic acid (50 mL), cobalt acetate (0.97 g), manganese acetate (0.98 g), and methyl ethyl ketone (1.90 mL) was placed in a 100 mL reactor and subjected to 1000 psi oxygen at 120° C. for 3.5 hours. The sample was spotted on TLC plates (K5F Whatman) and developed in 1:1 EtOAc/hexane and visualized under UV light. Visual analysis indicated that after 3.5 hours, substantially all of the HMF was converted. The reaction mixture (58.58 g) was found to contain 46,356 g/kg DFF (86%), 2,908 g/kg FFCA (5%), 4,201 g/kg HMF (8%) and 62 g/kg FDCA (1%) for a DFF selectivity of 86%. Subsequent GC/MS data revealed the conversion of HMF to DFF m/z=124. Thus, after 3.5 hours, the conversion of HMF to DFF was essentially complete.

Example 2

A reaction mixture containing 97% purity HMF (5.08 g), acetic acid (50 mL), cobalt acetate (0.973 g), manganese acetate (0.982 g), and methyl ethyl ketone (0.89 mL) was placed in a 100 mL reactor and subjected to 1000 psi oxygen at 120° C. for 4.5 hours. The reaction mixture (49.76 g) contained 41,368 mg/kg DFF (87%), 3,344 mg/kg FFCA, 2,671 mg/kg HMF and 32 mg/kg FDCA. Product selectivity of DFF was 87%. GC/MS data revealed complete conversion to DFF m/z=124. Acetic acid was removed and the product extracted with methyl isobutyl ketone. Substantially pure DFF (92% purity) was recovered.

Example 3

A reaction mixture containing 97% purity HMF (10.04 g), acetic acid (50 mL), cobalt acetate (1.94 g), manganese acetate (1.94 g), and methyl ethyl ketone (1.78 mL) was placed in a 100 mL reactor and subjected to 1000 psi oxygen at 120° C. for 4 hours. Samples were taken at 2 and 4 hours and analyzed by LCMS.

| Time (h) | FDCA (mg/kg) | FFCA (mg/kg) | HMF (mg/kg) | DFF (mg/kg) |
| --- | --- | --- | --- | --- |
| 2 | 3,939 | 2,221 | 14,729 | 39,179 |
| 4 | 1,021 | 7,544 | 7,729 | 73,737 |

As is shown, after 4 hours, the reaction mixture (64.17 g) was found to contain 73,737 mg/kg DFF (82%), 7,544 mg/kg (8.3%) FFCA, 1,021 mg/kg FDCA (1.1%) and 7,729 mg/kg HMF (8.6%). GC/MS analysis revealed the essentially complete conversion to DFF with a parent ion at m/z=124.

Oxidation of HMF to FDCA

Example 4

A reaction mixture containing 97% purity HMF (5.02 g), acetic acid (70 mL), cobalt acetate (0.165 g), manganese acetate (0.169 g), and sodium bromide (0.142 g) was placed in a 100 mL reactor and subjected to 800 psi oxygen at 100°

C. for 5 hours. Analysis (GC/MS and ¹H NMR) of the solid precipitate (2.40 g) revealed substantially pure FDCA. The yield of FDCA based on the amount of precipitated solid was 49% (mol/mol) of the HMF, however, no analysis was done on material that remained in the filtrate solution.

Example 5

A reaction mixture containing 97% purity HMF (10 g), acetic acid (50 mL), cobalt acetate (0.248 g), manganese acetate (0.248 g), and sodium bromide (0.208 g) was placed in a 100 mL reactor and subjected to 800 psi oxygen at 100° C. for 4 hours. The solid precipitate was removed by filtration. Analysis (GC/MS and 1H NMR) of the solid precipitate (5.21 g) again revealed substantially pure FDCA. The yield of FDCA based on the amount of precipitated solid was 48% (mol/mol) of the HMF. The filtrate (59.18 g) contained 44142 mg/kg FDCA, 4385 mg/kg FFCA and 193 mg/kg DFF.

Oxidation of HMF to FDCA Using Only Co Catalyst

Example 6

A reaction mixture containing 97% purity HMF (5.0 g), acetic acid (50 mL), cobalt acetate (0.97 g) and methyl ethyl ketone (0.89 mL) was placed in a 100 mL reactor and subjected to 1000 psi oxygen at about 120° C. for 4 hours.

| Time (h) | FDCA (mg/kg) | FFCA (mg/kg) | HMF (mg/kg) | DFF (mg/kg) |
|---|---|---|---|---|
| 2 | 4969 | 5247 | 3109 | 1883 |
| 4 | 8555 | 5946 | 257 | 1178 |

After 4 hours, substantially all of the HMF was converted. The selectivity of FDCA was 54%. In this system, cobalt was the only catalyst, suggesting that the oxidation can be driven to FDCA without the need for a metal co-catalyst or bromide promoter.

Non Selective Oxidation of HMF to Carboxylic Acids

Example 7

A reaction mixture containing 97% purity HMF (5.02 g), acetic acid (50 mL), cobalt acetate (0.97 g), manganese acetate (0.98 g), and methyl ethyl ketone (1.90 mL) was placed in a 100 mL reactor and subjected to 1000 psi oxygen at a temperature that varied between 120-140° C. for 3 hours.

| Time (h) | FDCA (mg/kg) | FFCA (mg/kg) | HMF (mg/kg) | DFF (mg/kg) |
|---|---|---|---|---|
| 1 | 7153 | 7573 | 4182 | 5254 |
| 2 | 10688 | 14804 | 3528 | 9041 |
| 3 | 24619 | 13241 | 826 | 4928 |

After 3 hours, essentially complete conversion of HMF had occurred with the reaction mixture containing 24619 mg/kg FDCA (56%), 13241 mg/kg FFCA (30%), 826 mg/kg HMF (2%), and 4928 mg/kg DFF (11%). As is shown, product selectivity is less predictable and favors the formation of carboxylic acids when the temperature was not maintained at 120° C. or less.

Example 8

A reaction mixture containing 97% purity HMF (5.02 g), acetic acid (50 mL), cobalt acetate (0.97 g), manganese acetate (0.98 g), and methyl ethyl ketone (0.85 mL) was placed in a 100 mL reactor and subjected to 1000 psi oxygen that varied between 120-140° C. for 6 hours.

| Time (h) | FDCA (mg/kg) | FFCA (mg/kg) | HMF (mg/kg) | DFF (mg/kg) |
|---|---|---|---|---|
| 1.5 | 1198 | 3659 | 14324 | 26642 |
| 2.5 | 1920 | 14744 | 3692 | 21126 |
| 4.5 | 1979 | 17496 | 1399 | 18434 |
| 6 | 5486 | 20882 | 974 | 19261 |

After 6 hours, essentially complete conversion of HMF has occurred with the reaction mixture containing 5486 mg/kg FDCA (11%), 20882 mg/kg FFCA (45%), 974 mg/kg HMF (2%), and 19261 mg/kg DFF (41%). As is shown, product selectivity decreases significantly when the temperature was not maintained to 120° C. or less.

Selective Oxidation of HMF to FDCA Using Co/Ce Catalysts

Example 9

A reaction mixture containing 97% purity HMF (5 g), acetic acid (50 mL), cobalt acetate (0.165 g), cerium acetate (0.162 g), and sodium bromide (0.142 g) was placed in a 100 mL reactor and subjected to 400 psi oxygen at 100° C. for 1.5 hours. A precipitate was formed. Samples of the liquid were taken every 30 minutes and subjected to LCMS analysis.

| Time (h) | FDCA (mg/kg) | FFCA (mg/kg) | HMF (mg/kg) | DFF (mg/kg) |
|---|---|---|---|---|
| 0.5 | 373 | 768 | 18547 | 4027 |
| 1.0 | 9031 | 694 | 2731 | 1025 |
| 1.5 | 7924 | 438 | 532 | 406 |

As is shown, after 1.5 hours, the conversion of HMF to FDCA was essentially complete. The solid precipitate (2.37 g) was substantially pure FDCA as characterized by ¹H NMR.

Synthesis of DFF from HMF Using Air

Example 10

A reaction mixture containing 97% purity HMF (5.00 g), acetic acid (50 mL), cobalt acetate (0.97 g), manganese acetate (0.97 g), and methyl ethyl ketone (0.89 mL) was placed in a 100 mL reactor and subjected to 1000 psi air at 115 C for 4 hours. A sample taken at 4 hours was subjected to TLC analysis as described in example 1. Visual analysis indicated partial conversion of HMF to DFF and the AcHMF ether. The temperature was then increased to 125 C for an additional 2 hours. The catalysts were removed by filtration and the solvent evaporated. The product was washed with water to give a cream colored solid. ¹H NMR analysis of the isolated solid indicated a 1:1 mixture of DFF and 5-acetoxymethylfurfural with essentially complete conversion of HMF. NMR ($\delta$, 1H): 10.2 (s, 2.0 H) DFF; 7.82 (s, 2.0 H) DFF; 9.84 (s, 1.0H)

AcHMF; 7.86 (d, 1H) AcHMF; 6.98 (d, 1H) AcHMF; 5.42 (s, 2H) AcHMF; 2.42 (s, 3H) AcHMF.

Purification of DFF from Reaction Mixture

Example 11

This example illustrates a simple method of DFF purification. A reaction mixture that was obtained from example 1, was allowed to evaporate. The resulting material was dissolved in diethyl ether with heating and the liquid was decanted from the black waxy material. The ether solution was cooled and a precipitate formed. The precipitate was removed by filtration and dried under vacuum. $^1$H NMR analysis indicates substantially pure DFF. NMR (δ, 1H): 7.40 (s, 2.0 H); 9.80 (s, 2.0 H). GC/MS: m/z=124.

Effect of High Temperature on Oxidation of HMF to FFCA and DFF

Example 12

A reaction mixture containing 97% purity HMF (10 g), acetic acid (50 mL), cobalt acetate (1.94 g), manganese acetate (1.94 g), and methyl ethyl ketone (1.78 mL) was placed in a 100 mL reactor and subjected to 1000 psi oxygen at about 130° C. for 5 hours. Samples were taken at 2, 4 and 5 hours.

| Time (h) | FDCA (mg/kg) | FFCA (mg/kg) | HMF (mg/kg) | DFF (mg/kg) |
|---|---|---|---|---|
| 2 | 854 | 4951 | 30779 | 19849 |
| 4 | 1579 | 16731 | 3694 | 44072 |
| 5 | 2292 | 27035 | 4151 | 64251 |

As is shown, after 5 hours, the reaction mixture contained 2292 mg/kg FDCA (2%), 27035 mg/kg FFCA (28%), 4151 mg/kg HMF (4%), and 64251 mg/kg DFF (66%). Thus, temperature was found to effect product selectivity.

Oxidation of BMF to Ester Acid Derivative

Example 13

A reaction mixture containing 82% butoxymethylfurfural (6.12 g), acetic acid (70 mL), cobalt acetate (0.165 g), manganese acetate (0.169 g), and sodium bromide (0.142 g) was placed in a 100 mL reactor and subjected to 1000 psi oxygen at 100° C. for 5 hours. GC/MS data revealed complete conversion of BMF, with the predominant product being the ester/acid 5-(butoxycarbonyl)furan-2-carboxylic acid m/z=157, 139, 56.

Example 14

A reaction mixture containing 80% butoxymethylfurfural (12.19 g), acetic acid (50 mL), cobalt acetate (0.165 g), manganese acetate (0.165 g), and sodium bromide (0.142 g) was placed in a 100 mL reactor and subjected to 600 psi oxygen at 100° C. for 5 hours. Samples were taken at 0.5 and 1 h and analyzed by TLC as described in example 1. Visual analysis of TLC plate with UV light indicated that after 1 h, essentially all of the BMF was converted to 5-(butoxycarbonyl)furan-2-carboxylic acid. GC/MS analysis confirmed these results (m/z 157, 139, 56. After the reaction was completed, the precipitated solid was removed by filtration and analyzed by $^1$H NMR. Substantially pure 5-(butoxycarbonyl)furan-2-carboxylic acid (1.88 g) was recovered.

Oxidation of AcHMF to FDCA

Example 15

A reaction mixture containing acetoxymethylfurfural (5.0 g), acetic acid (50 mL), cobalt acetate (0.13 g), manganese acetate (0.13 g), and sodium bromide (0.11 g) was placed in a 100 mL reactor and subjected to 500 psi oxygen at 100 C for 2 hours. The solid (2.53 g) was removed by filtration to give a 54% molar yield of FDCA from AcHMF and a 5-(xcetoxymethyl)furan-2-carboxylic acid (AcMFCA) by-product.

Purification of Oxidized BMF from Reaction Mixture

Example 16

A reaction mixture that was obtained from example 5, was allowed to evaporate. The resulting material was placed in a mixture of water (25 mL) and ethyl acetate (25 mL). A solution of 4.0M HCl in dioxane was added dropwise to lower the pH to <2. The two layers were allowed to separate. The aqueous layer was washed with ethyl acetate and the organic layers combined and dried over $MgSO_4$. Following filtration of the $MgSO_4$, the solvent was removed by rotary evaporation. $^1$H NMR and GC/MS data revealed conversion of BMF to the ester/acid m/z=157, 139, 56 in high purity (>90%).

While this invention has been described with reference to several preferred embodiments, it is contemplated that various alterations and modifications thereof will become apparent to those skilled in the art upon a reading of the preceding detailed description. It is therefore intended that the following appended claims be interpreted as including all such alterations and modifications

We claim:

1. A method of oxidizing furan aldehydes comprising heating the furan aldehyde in a reaction mixture comprising a solvent containing dissolved oxygen and at least one catalyst selected from the group consisting of Co(II), Mn(II), Ce(III) and salts thereof, wherein:
   (i) if the furan aldehyde is -5-(hydroxymethyl)furfural, the reaction mixture comprises an aliphatic ketone and a predominant reaction product of the oxidizing is diformylfuran; OR
   (ii) if the furan aldehyde is a 5-ether of the furan aldehyde, the predominant reaction product is at least one of a 5-ester furan 2-acid and a 5-(alkoxycarbonyl)furfural; OR
   (iii) if the furan aldehyde is a 5-(alkoxycarbonyl)furfural the predominant reaction product is a 5-ester furan 2-carboxylic acid; OR—
   (iv) if the furan is a 5-(alkoxymethyl)furoic acid the product is a 5-ester furan 2-carboxylic acid.

2. The method of claim 1, wherein the 5-ether of the furan aldehyde is selected from the group consisting of: a 5-(alkoxymethyl)furfural, a 5-(aryloxymethyl)furfural, and a 5-(cycloalkoxy-methyl)furfural.

3. The method of claim 1, wherein the furan aldehyde is 5-(hydroxymethyl)furfural.

4. The method of claim 1, wherein the 5-ether of the furan aldehyde is selected from the group consisting of 5-(acetoxymethyl)furfural and 5-(butoxymethyl)furfural.

5. The method of claim 1, wherein the reaction mixture is heated to a temperature of between 80° C. and 130° C. at a pressure of oxygen or air of about 800- to about 1000 psi for a time sufficient to form the predominant reaction product.

6. The method of claim 5, wherein the temperature is between 100° C. and 125° C.

7. The method of claim 5, wherein the pressure is the pressure of oxygen.

8. The method of claim 1 wherein the reaction mixture contains acetic acid as a principle solvent.

9. The method of claim 1 wherein at least 90% of the furan aldehyde is oxidized into reaction products, and the predominant reaction product is at least 80% of the reaction products.

10. The method of claim 1 wherein the predominant reaction product is a 5-ester furan 2-carboxylic acid and is collected as a precipitate from the reaction mixture in a first purification step.

11. The method of claim 10 wherein the precipitate is dissolved in a solvent in which the predominant product has higher solubility than FDCA in a second purification step.

12. The method of claim 11 wherein the solvent is selected from the group consisting of ethyl acetate, dimethylformamide, dimethylacetamide, tetrahydrofuran, dioxane, methyl ethyl ketone, acetonitrile, methyltetrahydrofuran, ethyl isobutyl ketone, and C1-C6 alcohols.

13. The method claim 1 wherein the at least one catalyst salt has an anion selected from the group consisting of an acetate, acetate hydrate, bromide, chloride, fluoride, iodide, alkoxide, azide, oxalate, carbonate, carboxylate, hydroxide, nitrate, borate, oxide, acetylacetonate and mixtures thereof.

14. The method of claim 1, wherein the reaction mixture comprises $CO_2$ expanded in a principle solvent of the reactions mixture.

15. The method of claim 14 wherein the principle solvent is acetic acid.

16. The method of claim 14 wherein the $CO_2$ is expanded in the solvent at a pressure of at least 100 psi.

17. The method of claim 14 wherein the oxygen is provided by oxygen gas or air dissolved in the solvent at a pressure of at least 200 psi and $CO_2$ is expanded in the solvent at a pressure of at least 100 psi.

18. The method of claim 1 wherein the reaction mixture also comprises bromide and FDCA is formed as co product of the oxidizing.

19. The method of claim 1 wherein the furan aldehyde is -5-(hydroxymethyl)furfural, the predominant reaction product is diformyl furan, and the reaction mixture does not contain bromide.

* * * * *